(12) United States Patent
Koehler et al.

(10) Patent No.: US 12,427,277 B2
(45) Date of Patent: Sep. 30, 2025

(54) IMAGING-BASED SIZING OPTIMIZATION OF ENDOTRACHEAL TUBE FOR MECHANICAL VENTILATION

(71) Applicant: KONINKLIJKE PHILIPS N.V., Eindhoven (NL)

(72) Inventors: Thomas Koehler, Hamburg (DE); Rafael Wiemker, Hamburg (DE); Cornelis Petrus Hendriks, Eindhoven (NL); Joerg Sabczynski, Hamburg (DE); Kiran Hamilton J. Dellimore, Eindhoven (NL); Michael Polkey, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 818 days.

(21) Appl. No.: 17/738,326

(22) Filed: May 6, 2022

(65) Prior Publication Data
US 2022/0401678 A1 Dec. 22, 2022

Related U.S. Application Data

(60) Provisional application No. 63/213,247, filed on Jun. 22, 2021.

(51) Int. Cl.
*A61M 16/04* (2006.01)
*A61B 1/267* (2006.01)
(Continued)

(52) U.S. Cl.
CPC ......... *A61M 16/0488* (2013.01); *A61B 1/267* (2013.01); *A61B 6/032* (2013.01); *A61B 6/5247* (2013.01); *G06T 7/0012* (2013.01); *G06T 7/174* (2017.01); *A61B 2090/364* (2016.02); *G06T 2207/10081* (2013.01)

(58) Field of Classification Search
None
See application file for complete search history.

(56) References Cited

U.S. PATENT DOCUMENTS 6,705,319 B1 * 3/2004 Wodicka ............... A61M 25/01
128/207.14
8,721,589 B1 * 5/2014 Stanhope ............ A61M 16/044
604/99.02
(Continued)

FOREIGN PATENT DOCUMENTS

WO 9836683 A1 8/1998

OTHER PUBLICATIONS

International Search Report for PCT/EP2022/065957 filed Jun. 13, 2022.
(Continued)

*Primary Examiner* — Helen Zong
(74) *Attorney, Agent, or Firm* — Daniel H. Brean

(57) ABSTRACT

An intubation assistance device includes an electronic controller configured to: identify, from one or more images of a patient, information about the patient including at least a diameter of a trachea and a length of an intubation pathway; determine a recommended ETT size including an ETT diameter and an ETT depth of insertion from the determined diameter of the trachea and the determined length of the intubation pathway; and display the recommended ETT size on a display device.

8 Claims, 3 Drawing Sheets

(51) Int. Cl.
  *A61B 6/00*    (2024.01)
  *A61B 6/03*    (2006.01)
  *A61B 90/00*   (2016.01)
  *G06T 7/00*    (2017.01)
  *G06T 7/174*   (2017.01)

(56) References Cited

U.S. PATENT DOCUMENTS

| | | | |
|---|---|---|---|
| 2012/0197086 A1 | 8/2012 | Morris | |
| 2015/0196228 A1 | 7/2015 | Akimoto | |
| 2016/0022943 A1* | 1/2016 | Kanowitz | A61B 1/00165 128/207.14 |
| 2020/0315770 A1 | 10/2020 | Dupont | |
| 2022/0171890 A1* | 6/2022 | Bergounioux | G06F 30/10 |

OTHER PUBLICATIONS

Gupta, K. et al. "Assessment of the subglottic region by ultrasonography for estimation of appropriate size endotracheal tube: A clinical prospective study". Anesthesia, Essays and Research India, vol. 6, No. 2, (2013), p. 157.

Cherng, C-H et al., "Airway length in adults: estimation of the optimal endotracheal tube length for orotracheal intubation", vol. 14, No. 4, (2002), pp. 271-274.

Zhu, C. et al., "Automatic 3D segmentation of human airway tree in CT image." IEEE Conference Publication, IEEE Xplore, (2010). doi: 10.1109/BMEI.2010.5639658.

Meng, Q. et al., "Automatic segmentation of airway tree based on local intensity filter and machine learning technique in 3D chest CT volume." (2017) SpringerLink, doi: 10.1007/s11548-016-1492-2.

Reynisson, P.J. et al., "Airway Segmentation and Centerline Extraction from Thoracic CT—Comparison of a New Method to State of the Art Commercialized Methods." (PLOS.org), (2015). doi: 10.1371/journal.pone.0144282.

Galibourg, A. et al., "Assessment of automatic segmentation of teeth using a watershed-based method." Dentomaxillofacial Radiology (2018). doi: 10.1259/dmfr.20170220.

Cui, Z. et al., "ToothNet: Automatic Tooth Instance Segmentation and Identification From Cone Beam CT Images." (researchgate.net), (2019). doi: 10.1109/CVPR.2019.00653.

Akhoondali, H. et al., Rapid Automatic Segmentation and Visualization of Teeth in CT-Scan Data (scialert.net), DOI: 10.3923/jas.2009.2031.2044.

McCulloch, M.M. et al., "Biomechanical modelling of neck flexion for deformable alignment of the salivary glands in head and neck cancer images", Phys Med Biol. Sep. 5, 2019;64(17):175018. doi: 10.1088/1361-6560/ab2f13.

Endotracheal Tube Size Calculator, OmniCalculator, https://www.omnicalculator.com/health/ett-size.

FAST Integrated Workflow (siemens-healthineers.com).

* cited by examiner

IMAGING-BASED SIZING OPTIMIZATION OF ENDOTRACHEAL TUBE FOR MECHANICAL VENTILATION

CROSS-REFERENCE TO RELATED APPLICATIONS

This application claims the priority benefit under 35 U.S.C. § 119(e) of U.S. Provisional Application No. 62/213,247, filed on Jun. 22, 2021, the contents of which are herein incorporated by reference.

The following relates generally to the respiratory therapy arts, tracheal intubation arts, endotracheal tube sizing arts, and related arts.

BACKGROUND

Mechanical ventilation of a patient typically entails placement of an endotracheal tube (ETT) into a trachea of the patient, in a process known as tracheal intubation. The desired position of the tip of an ETT is approximately 5.0 cm (±2.0 cm) above a carina (i.e., a location where the trachea splits into the main right and left bronchi). Tracheal intubation is usually performed by an anesthesiologist or other qualified medical professional, and in a common sequence the head is moved backward to access the airway, and a laryngoscope is used to facilitate proper placement of the ETT between the vocal cords and into the trachea, without misplacement into the esophagus.

Common situations where mechanical ventilation is required can include intensive care unit (ICU) cases and during major surgery. Such patients often have images (i.e., computed tomography (CT) images) obtained of the thorax before being sent to the ICU, in particular if the patient's condition is a lung-related disease (e.g., Covid-19), or trauma.

However, the ETT may be incorrectly positioned (such as in the esophagus or one of the bronchi), or there may be an air-leak in the ETT. Although uncommon, when these situations occur, it may lead to severe complications with long term consequences due to cerebral hypoxia.

An important consideration when intubating a patient is proper selection of the ETT size. ETTs are available in various sizes, e.g., from 2 mm to 10.5 mm internal diameter in some sizing schemes, with the smallest sizes being used for intubating infants. For patients older than one year, one formula for selecting the internal diameter in millimeters is Age+16/4. In addition to selecting ETT diameter, the depth of insertion of the ETT is another important sizing parameter. The end of the ETT is preferably positioned above the carina, that is, where the trachea branches into the left and right bronchial tubes leading into the respective lungs, in order to ensure a well-sealed fit while ventilating both the left and right lungs equally. The ETT usually has marks along its length (e.g., tic marks every 1 cm or the like) so that the tube insertion depth can be tracked visually during the tracheal intubation process. A formula for selecting the depth of insertion in centimeters is Age+12/2 While these are general rules, patient-specific anatomy can significantly impact ETT sizing (optimal tube diameter and depth of insertion), as well as the difficulty in performing the tracheal intubation. Improper tracheal intubation can lead to serious complications, such as perforation of the trachea (or of the esophagus if the ETT is misplaced), nerve damage, spinal damage, vocal cord damage, inadequate mechanical ventilation via the inserted ETT, bronchial intubation (insertion of the ETT too deeply so that it enters the left or right bronchial tube), accidental dislodgment of the ETT, and so forth. Performing the tracheal intubation with a tube of the wrong size can directly or indirectly lead to many such complications. Intubation with an ETT of too-small diameter can lead to inadequate ventilation and possible dislodgement; whereas, using a too-large diameter can lead to excessive force being applied to the airway potentially leading to damage to nerves, vocal cords, or other airway tissue. Similarly, insufficient depth of insertion can lead to inadequate ventilation and possible dislodgement, whereas excessive depth of insertion can lead to bronchial intubation. The laryngoscope permits visual observation only of the upper airway structures (glottis and larynx), so that tracheal intubation is a partially "blind" procedure.

The following discloses certain improvements to overcome these problems and others.

SUMMARY

In one aspect, an intubation assistance device includes an electronic controller configured to: identify, from one or more images of a patient, information about the patient including at least a diameter of a trachea and a length of an intubation pathway; determine a recommended ETT size including an ETT diameter and an ETT depth of insertion from the determined diameter of the trachea and the determined length of the intubation pathway; and display the recommended ETT size on a display device.

In another aspect, an intubation assistance method includes, using an electronic controller: identifying, from one or more images of a patient, information about the patient including at least a diameter of a trachea and a length of an intubation pathway; determining a recommended ETT size including an ETT diameter and an ETT depth of insertion from the determined diameter of the trachea and the determined length of the intubation pathway; and displaying the recommended ETT size on a display device.

One advantage resides in providing mechanical ventilation therapy to a patient with an ETT of suitable diameter sizing inserted into the patient's trachea.

Another advantage resides in providing mechanical ventilation therapy to a patient with an ETT of suitable insertion depth sizing into the patient's trachea.

Another advantage resides in determining a suitable size of the ETT that takes into account the individualized anatomy of the patient.

Another advantage resides in determining a suitable ETT size for a patient based on one or more images of the patient.

Another advantage resides in using one or more models of the ETT and/or a patient geometry of the patient to determine a suitable size of the ETT.

Another advantage resides in using one or more models of the ETT and/or a patient geometry of the patient to determine an insertion depth of the ETT into the patient's trachea.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
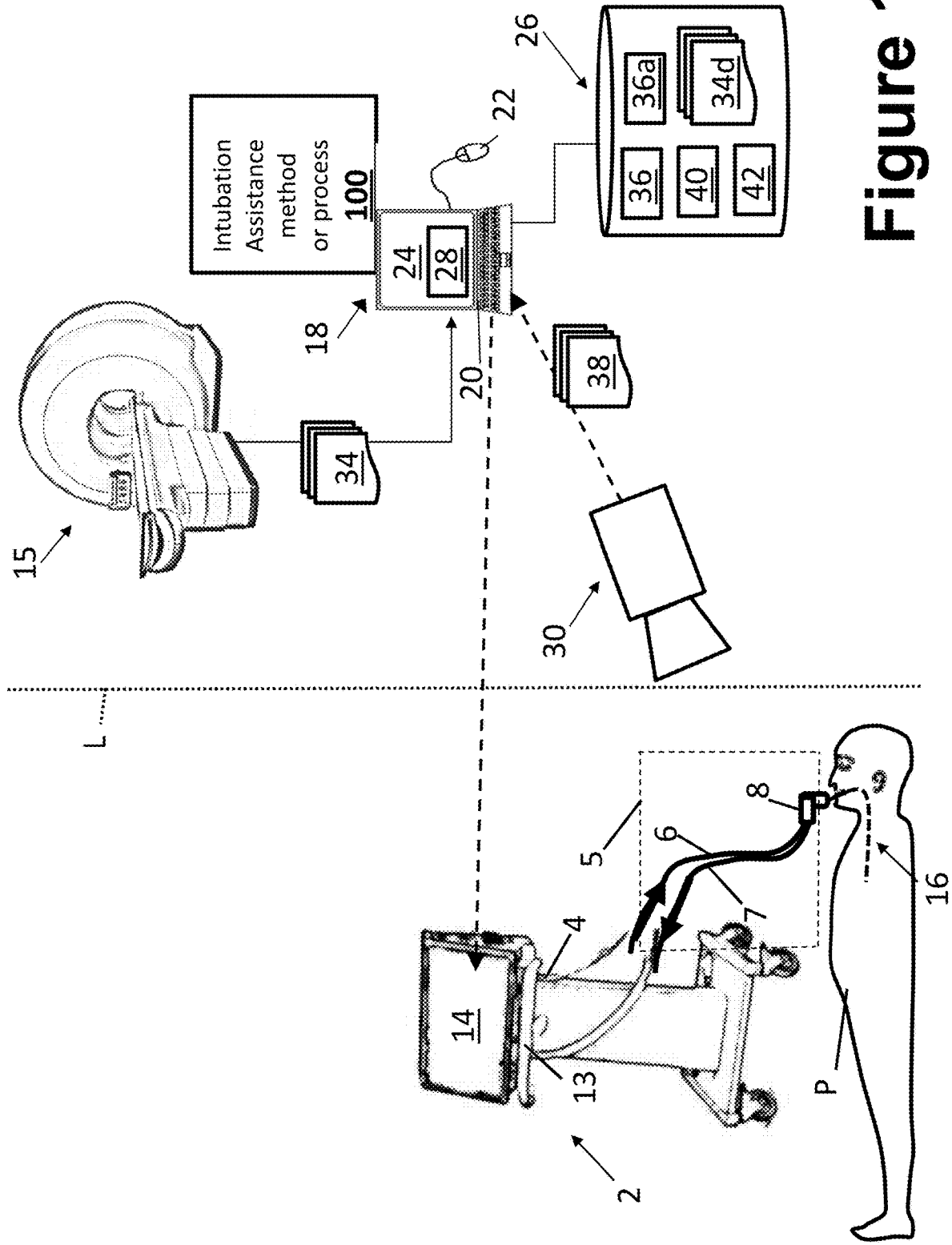
FIG. 1 diagrammatically shows an illustrative mechanical ventilation-imaging system in accordance with the present disclosure.

As used herein, the singular form of "a", "an", and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware.

With reference to FIG. 1, a mechanical ventilator 2 for providing ventilation therapy to an associated patient P is shown. As shown in FIG. 1, the mechanical ventilator 2 includes an outlet 4 connectable with a patient breathing circuit 5 to deliver mechanical ventilation to the patient P. The patient circuit 5 includes typical components for a mechanical ventilator, such as an inlet line 6, an optional outlet line 7 (this may be omitted if the ventilator employs a single-limb patient circuit), a connector or port 8 for connecting with an ETT, and one or more breathing sensors (not shown), such as a gas flow meter, a pressure sensor, end-tidal carbon dioxide ($etCO_2$) sensor, and/or so forth. The mechanical ventilator 2 is designed to deliver air, an air-oxygen mixture, or other breathable gas (supply not shown) to the outlet 4 at a programmed pressure and/or flow rate to ventilate the patient via an ETT.

FIG. 1 also shows a medical imaging device 15 (also referred to as an image acquisition device, imaging device, and so forth). The image acquisition device 15 can be a Computed Tomography (CT) image acquisition device, a C-arm imager, or other X-ray imaging device; Magnetic Resonance (MR) image acquisition device; an ultrasound (US) image acquisition device; or a medical imaging device of another modality. As primarily described herein, the medical imaging device 15 comprises a CT medical imaging device 15. As described herein, the medical imaging device 15 is used to acquire images of the patient P based upon which ETT sizing is performed. It should be noted that the imaging device 15 may not be located in the same room, or even the same department, as the mechanical ventilator 2. For example, the medical imaging device 15 may be located in a radiology laboratory while the mechanical ventilator 2 may be located in an intensive care unit (ICU), cardiac care unit (CCU), in a hospital room assigned to the patient P, or so forth. This is diagrammatically indicated in FIG. 1 by separator line L.

FIG. 1 diagrammatically illustrates the patient P intubated with an endotracheal tube (ETT) 16 (the lower portion of which is inside the patient P and hence is shown in phantom). The connector or port 8 connects with the ETT 16 to operatively connect the mechanical ventilator 2 to deliver breathable air to the patient P via the ETT 16. The mechanical ventilation provided by the mechanical ventilator 2 via the ETT 16 may be therapeutic for a wide range of conditions, such as various types of pulmonary conditions like emphysema or pneumonia, viral or bacterial infections impacting respiration such as a COVID-19 infection or severe influenza, cardiovascular conditions in which the patient P receives breathable gas enriched with oxygen, or so forth.

FIG. 1 shows the patient P already intubated. That is, FIG. 1 shows the patient after a tracheal intubation has been performed to insert the ETT 16 into the patient. However, to safely perform the tracheal intubation, the anesthesiologist or other qualified medical professional first performs an assessment of the patient P to select the ETT size of the ETT 16, and then inserts an ETT of the selected size into the patient P by a tracheal intubation procedure.

As a further note, as used herein the "ETT size" includes an ETT diameter and a depth of insertion. The length of the ETT 16 is longer than the depth of insertion, and the depth of insertion is not a characteristic metric of the ETT per se. However, the depth of insertion is typically determined for a given patient prior to performing the tracheal intubation. Thus, the ETT sizing for the patient P includes sizing both the ETT diameter and the depth of insertion. That is, the ETT size as used herein includes a tube diameter (specified by an inner diameter (ID) an outer diameter (OD), or both an ID and an OD) and a depth of insertion.

FIG. 1 further shows an intubation assistance device 18 configured to assist with intubation of the ETT 16 by providing a recommended ETT size (e.g., diameter and depth of insertion) prior to performing the tracheal intubation. The intubation assistance device 18 can comprise an electronic processing device, such as a workstation computer (more generally, a computer), a smart device (e.g., a smartphone, a tablet, and so forth), or server computer or a plurality of server computers, (e.g., interconnected to form a server cluster, cloud computing resource, or so forth). The intubation assistance device 18 includes typical components, such as an electronic controller 20 (e.g., an electronic processor or a microprocessor), at least one user input device (e.g., a mouse, a keyboard, a trackball, a finger swipe on a touchscreen of a smart device, and/or the like) 22, and at least one display device 24 (e.g., an LCD display, plasma display, cathode ray tube display, and/or so forth). In some embodiments, the display device 24 can be a separate component from the electronic processing device 18. The display device 24 may also comprise two or more display devices.

The electronic controller 20 is operatively connected with one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the intubation assistance device 18, various combinations thereof, or so forth. It is to be understood that any reference to a non-transitory medium or media 26 herein is to be broadly construed as encompassing a single medium or multiple media of the same or different types. Likewise, the electronic controller 20 may be embodied as a single electronic processor or as two or more electronic processors. The non-transitory storage media 26 stores instructions executable by the at least one electronic controller 20. The instructions include instructions to generate a graphical user interface (GUI) 28 for display on the remote operator display device 24.

In some embodiments, one or more cameras are disposed in an area where the medical imaging device 15 is located. For example, as shown in FIG. 1, a three-dimensional (3D) camera 30 can be positioned to image the patient P. Although only one 3D camera 30 is shown in FIG. 1, any suitable number of 3D cameras 30 can be used. Any suitable 3D camera 30 can be used (see, e.g., FAST Integrated Workflow (siemens-healthineers.com)).

Furthermore, as disclosed herein, the non-transitory storage media 26 stores instructions executable by the at least one electronic controller 20 to perform an intubation assistance method or process 100 determining a suitable size and/or insertion depth of the ETT 16 to be used with the mechanical ventilator 2 to provide ventilation therapy to the patient P.

It will be appreciated that, as previously noted, the mechanical ventilator 2 (and the 3D camera 30) can be disposed in a first room of a medical facility, while the image acquisition device 15 and the electronic processing device 18 can be disposed in a second, different room of the medical facility. This is depicted by the dashed line L in the generally "middle" portion of FIG. 1. In another example, the mechanical ventilator 2 and the electronic processing device 18 can be disposed in the first room, while the image acquisition device 15 is disposed in the second room of the medical facility. In a further example, each of the mechanical ventilator 2, the image acquisition device 15 and the electronic processing device 18 can be disposed in separate rooms of the medical facility. These are merely illustrative examples.

There may also be substantial temporal separation between (i) the acquisition of the images of the patient P using the imaging device 15 and determination of the ETT size recommendation for the patient P using the intubation assistance device 18, and (ii) the actual tracheal intubation of the patient P. For example, the patient P may first be transported on a gurney to a radiology lab housing the imaging device 15 for imaging and ETT sizing, and then transported on the gurney from the radiology lab to the location of the mechanical ventilator 2. In some embodiments described herein, the temporal separation may be even larger than this. For example, if the patient P undergoes a thoracic CT examination for some routine or diagnostic medical purpose, then as disclosed herein the acquired images may be used for that routine or diagnostic medical purpose and may also be secondarily leveraged to generate an ETT recommendation that may be stored in the Electronic Health Record (EHR) or other medical record of the patient P. Thereafter, if at some point (possibly weeks, months, or even years later) the patient P comes under medical care and requires mechanical ventilation, the ETT recommendation can be retrieved from the EHR or other medical record of the patient P and referenced by the anesthesiologist or other qualified medical professional performing the tracheal intubation.

Figure 2:
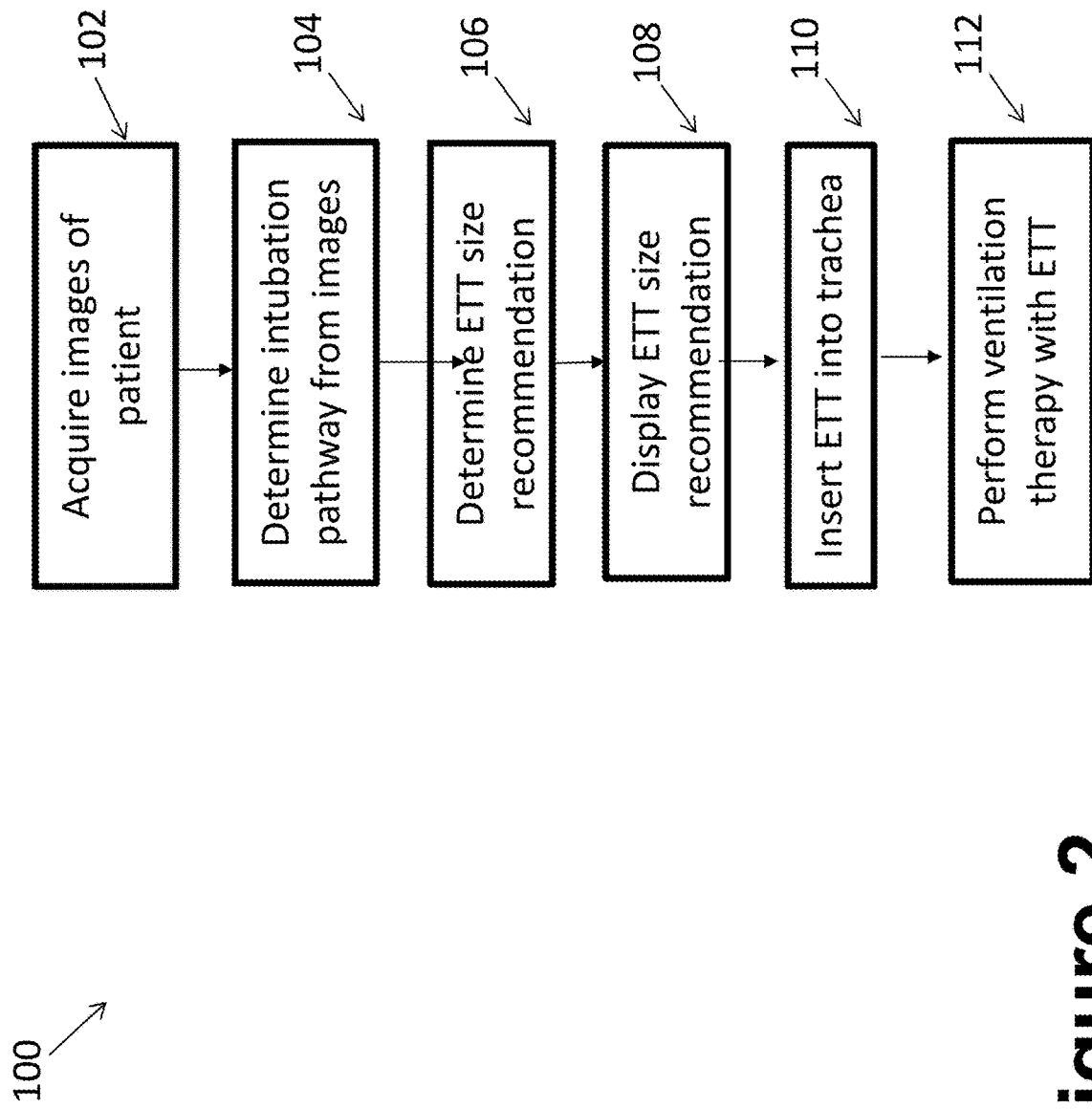
FIG. 2 shows an example flow chart of operations suitably performed by the system of FIGURE.

With reference to FIG. 2, and with continuing reference to FIG. 1, an illustrative embodiment of the intubation assistance method 100 is diagrammatically shown as a flowchart. At an operation 102, one or more images 34 of the patient are obtained by the medical imaging device 15. In a particular example, the acquired images 34 are CT images 34. In some examples, to acquire the CT images 34, the electronic controller 20 is configured to control the medical imaging device 15 (i.e., a CT scanner) to acquire the CT images 34 of the upper airway (e.g., from the mouth to the carina) of the patient P. In some embodiments, the electronic controller 20 is configured to control the medical imaging device 15 to acquire a diagnostic torso CT image of the patient P at a first Xray level, and an extended upper CT image extending upward from the diagnostic torso CT image of the patient P at a second Xray level that is lower than the first Xray level. In other embodiments, a single CT image 34 may be acquired along a patient axis that covers both the diagnostic torso CT image and the extended upper CT image. The electronic controller 20 is then configured to combine the diagnostic torso CT image and the extended upper CT image to generate the CT images 34 of the upper airway of the patient P. This approach of lowering the X-ray level for the extended upper CT image can be advantageous as the throat area, like other parts of the human anatomy, is sensitive to radiation damage, so that a lower X-ray level in this area provides lower dosage. Additionally, the amount of image detail required for performing the disclosed ETT sizing may be less than usually required for the diagnostic or screening task for which the torso CT examination was ordered, so that the lower X-ray level used for the extended upper CT image is sufficient for this purpose. This type of imaging sequence workflow may be particularly advantageous when performing the ETT sizing as a secondary result of a torso CT examination ordered for a specific diagnostic or screening task unrelated to ETT sizing.

At an operation 104, information about the patient P is identified from the acquired CT images 34. The identified information can include, for example, the upper airways of the patient P, a diameter of trachea of the patient P, and a length of an intubation pathway of the patient P. In some embodiments, the electronic controller 20 is configured to identify the upper airways of the patient P by segmenting the CT images 34 to identify an upper airway landmark (i.e., 5.0 cm above the carina), the trachea, and the carina of the patient. A length of the intubation pathway can be identified based on a distance from the upper airway landmark through the trachea to the carina of the patient P. In some examples, the segmentation might also include the centerline of the trachea. The segmentation can additionally provide a length measurement from the teeth to the point where the trachea and the esophagus enter the throat. This information might also be useful for a medical professional to select the depth of insertion of the ETT so as not to enter the esophagus during ETT placement. In other examples, a length starting from lips of the patient P to the carina is measured.

Any suitable segmentation algorithm can be used in performing the operation 104 (see, e.g., Automatic 3D segmentation of human airway tree in CT image|IEEE Conference Publication|IEEE Xplore, DOI: 10.1109/BMEI.2010.5639658; Automatic segmentation of airway tree based on local intensity filter and machine learning technique in 3D chest CT volume|SpringerLink, DOI 10.1007/s11548-016-1492-2; and Airway Segmentation and Centerline Extraction from Thoracic CT—Comparison of a New Method to State of the Art Commercialized Methods (plos.org), DOI 10.1371/journal.pone.0144282.

The identification of the length of the intubation pathway can also include identifying an entry point (i.e., the front teeth) for the ETT 16. The intubation pathway is identified from the front teeth to a desired endpoint (e.g., 5.0 cm above the carina). Any suitable algorithm can be used for this process (see, e.g., Assessment of automatic segmentation of teeth using a watershed-based method (nih.gov), doi: 10.1259/dmfr.20170220; ToothNet: Automatic Tooth Instance Segmentation and Identification From Cone Beam CT Images (researchgate.net), DOI: 10.1109/CVPR.2019.00653; and Rapid Automatic Segmentation and Visualization of Teeth in CT-Scan Data (scialert.net), DOI: 10.3923/jas.2009.2031.2044).

In some embodiments, during acquisition of the CT images 34, the head of the patient P may not be in a desired position (i.e., bent backwards, as is the usual positioning of the head during tracheal intubation). When this occurs, the electronic controller 20 is optionally configured to retrieve a patient anatomical model 36 (which contains the head and neck, and optionally at least the upper part of the thorax) from the non-transitory computer readable media 26. The electronic controller 20 may use the patient anatomical model 36 to deform the image of the head and neck of the patient P shown in the CT images 34 into a desired position resulting in deformed CT images 34d (e.g., with the head bent backwards). The patient anatomical model 36 represents the anatomy and, optionally biomechanical properties, of humans. The patient anatomical model 36 can be relatively simple (e.g., allowing an elastic deformation of the CT image(s) 34) or detailed (e.g., it can consider surrounding anatomical structures (e.g., rigid bones, contractable muscles, tendons, and soft tissue)). With respect to the head and neck part of the patient anatomical model 36, any suitable patient anatomical model 36 can be used (see, e.g., "Biomechanical modelling of neck flexion for deformable alignment of the salivary glands in head and neck cancer images", Phys Med Biol. 2019 Sep. 5; 64(17):175018. doi: 10.1088/1361-6560/ab2f13).

In other embodiments, the acquired CT images 34 do not depict at least a portion of the upper airway of the patient P (e.g., due to the patient P moving during image acquisition, the patient P being incorrectly positioned for imaging, and so forth). In such instances, the electronic controller 20 is configured to adapt or modify the patient anatomical model 36 based on one or more 3D images 38 of the patient P, acquired via the 3D camera 30. The 3D images 38 show an exterior (e.g., head and thorax) of the patient P. In one embodiment, the electronic controller 20 is configured to generate the 3D images 38 by generating a 3D model 40 from the CT images 34, and by generating the 3D images 38 of the exterior of the patient P from the 3D model 40. In another embodiment, the 3D images 38 of the exterior of the patient P are obtained by the 3D camera(s) 30 and transmitted to the electronic processing device 18. The electronic controller 20 is then configured to register the patient anatomical model 36 with the CT images 34 to obtain a hybrid imaging data set, which is used to determine the intubation pathway. The identifying information about the patient P is further based on the extracted patient anatomical model 36.

In other embodiments, the acquired CT images 34 do not depict at least a portion of the upper airway of the patient P (e.g., due to the patient P moving during image acquisition, the patient P being incorrectly positioned for imaging, and so forth). In such instances, the electronic controller 20 is configured to retrieve a patient anatomical (head, neck, and optionally thorax) model 36 from the non-transitory computer readable media 26. The electronic controller 20 is further configured to identify the region where the patient anatomical model 36 and the CT image 34 overlap and to adjust parameters of the model such that the adjusted patient anatomical model 36a fits in the overlapping region to the CT images 34. The electronic controller 20 is further configured to generate a hybrid imaging data set from the measured CT images 34 (where available) and the adjusted patient anatomical model 36a (where desired information from images 34 are missing). The hybrid imaging data set is subsequently used to determine the intubation pathway.

Once the intubation pathway is determined at the operation 104, the method 100 proceeds to an operation 106, in which the electronic controller 20 is configured to determine a recommended ETT size for the patient P from the determined diameter of the trachea and the determined length of the intubation pathway. To do so, an ETT model 42 can be retrieved from the non-transitory computer readable media 26. The electronic controller 20 is configured to use the ETT model 42 to determine a desired stiffness of the ETT 16 by inputting the determined diameter of the trachea and the determined length of the intubation pathway to the ETT model 42, which then outputs the recommended size of the ETT 16 for the patient P including a recommended depth of insertion of the ETT 16. The identification of the intubation pathway length is further based on the stiffness of the ETT 16. In some examples, since the center line of the trachea and the upper airway do not conform to the shape of the ETT 16, the ETT 16 may touch or contact a tracheal wall at different sides. The ETT model 42 can be used to account for a difference between the actual required depth of insertion of the ETT 16 and the length of the center line of the determined length of the intubation pathway.

At an operation 108, the recommended ETT size for the patient P is displayed, via the GUI 28, on the display device 24 of the electronic processing device 18. Additionally or alternatively, the recommended ETT size can be transmitted to the mechanical ventilator 2 for display on the display device 14 thereof. Advantageously, a medical professional in the room where the mechanical ventilator 2 can quickly see the recommended ETT size for the patient P on the mechanical ventilator 2.

At an operation 110, the ETT 16 having the recommended ETT size for the patient P is inserted into the trachea of the patient P. The medical professional can use markings conventionally included on the ETT 16 to determine progress of the insertion depth of the ETT. The ETT 16 is inserted into the trachea to the recommended depth of insertion so as to place the tip of the ETT 16 at a desired point (e.g., 5.0 cm above the carina). In some embodiments, a heads-up display (HUD), such as augmented reality (AR) glasses or headset (e.g., a Microsoft HoloLens, Bellevue, WA, United States) (not shown) can be used to guide the medical professional during placement (and subsequent removal) of the ETT 16. In particular, the AR device can be used to indicate the position of the ETT 16 in relation to relevant anatomical structures within the patient's body derived from the CT images 34 and/or from the patient anatomical model 36. This further aids in improving the accuracy of positioning of the ETT 16 and thereby decrease the risk of complications.

At an operation 112, the ETT 16 is connected to the mechanical ventilator 2 (e.g., at the port or connector 8). The medical professional then operates the mechanical ventilator 2 to deliver ventilation therapy to the patient P with the mechanical ventilator 2.

Since the information can be obtained from any thorax CT image 34 (optionally in combination with the patient anatomical model 36), the CT image acquisition and the ventilation therapy can be separated in time by days, weeks, months, or even years. For example, if a patient gets a thorax CT image 34 for some unrelated medical purpose, the optimal ETT size for the patient including the ETT diameter and depth of insertion can be calculated routinely and stored in the EHR (e.g., similar to a blood type of the patient). If the patient requires at any time later mechanical ventilation (e.g., after a car accident) then the information can be retrieved from the EHR. This may be particularly useful since the ETT 16 may be placed by an emergency medicine technician rather than a consultant anesthetist, and often in a situation where time pressures and clinical issues (e.g., blood in the airway) may make ETT placement more difficult.

Figure 3:
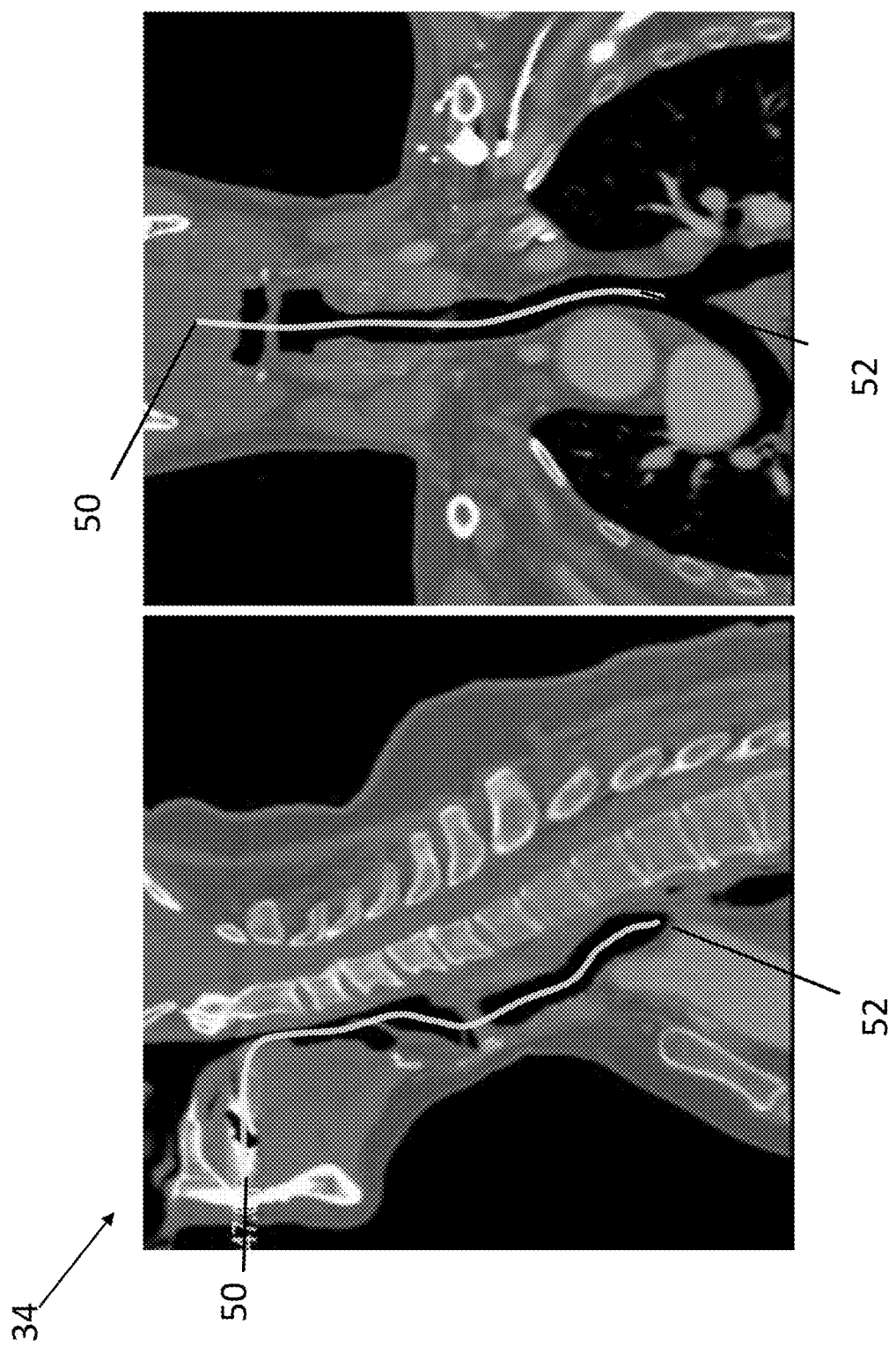
FIG. 3 shows an image with an intubation pathway determined by the system of FIG. 1.

FIG. 3 shows an example of the planning of the intubation pathway (e.g., operation 102) and the recommended size of the ETT 16 (e.g., operation 104). FIG. 3 shows side and front views of a CT image 34 of the patient's head and neck. The intubation pathway is shown in both views extends from the front teeth of the patient P (depicted by reference character 50) to the desired endpoint (depicted by reference character 52) (e.g., 5.0 cm above the carina).

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An intubation assistance device comprising an electronic controller configured to:
   identify, from one or more images of a patient, information about the patient including at least a diameter of a trachea and a length of intubation pathway;
   determine a recommended endotracheal tube (ETT) size including an ETT diameter and an ETT depth of insertion from the determined diameter of the trachea and the determined length of the intubation pathway; and
   display the recommended ETT size on a display device, wherein the electronic controller is configured to determine the ETT size by:
      using an ETT model to determine a stiffness of the ETT, the determination of the ETT depth of insertion being further based on the stiffness of the ETT.

2. An intubation assistance device comprising an electronic controller configured to:
   identify, from one or more images of a patient, information about the patient Including at least a diameter of a trachea and a length of an intubation pathway;
   determine a recommended endotracheal tube (ETT) size including an ETT diameter and an ETT depth of insertion from the determined diameter of the trachea and the determined length of the intubation pathway; and
   display the recommended ETT size on a display device, wherein the electronic controller is further configured to:
      adjust the one or more images with a patient anatomical model to deform the one or more images of the patient into a desired position, the information about the patient being identified from the adjusted one or more images.

3. An intubation assistance device comprising an electronic controller configured to:
   identify, from one or more images of a patient, information about the patient Including at least a diameter of a trachea and a length of an intubation pathway;
   determine a recommended endotracheal tube (ETT) size including an ETT diameter and an ETT depth of insertion from the determined diameter of the trachea and the determined length of the intubation pathway; and
   display the recommended ETT size on a display device,
   wherein the one or more images do not depict at least a portion of the upper airway of the patient and the electronic controller is further configured to:
      modify a patient anatomical model based on one or more images of an exterior of the patient;
      wherein the identifying information about the patient is further based on the patient anatomical model modified based on the one or more images of the exterior of the patient.

4. The intubation assistance device of claim 3, wherein the electronic controller is further configured to generate the one or more images of the exterior of the patient by:
   generating a 3D imaging model from the one or more images of the patient; and
   generating the one or more images of the exterior of the patient from the 3D imaging model.

5. The intubation assistance device of claim 3, wherein the images of the exterior of the patient are comprised of one or more 3D images acquired from one or more 3D cameras.

6. The intubation assistance device of claim 3, wherein the electronic controller is configured to:
   register the patient anatomical model extracted from the one or more images of the exterior of the patient with the one or more images to generate a hybrid imaging data set; and
   determine the intubation pathway based on the hybrid imaging data set.

7. An intubation assistance device comprising an electronic controller configured to:
   identify, from one or more images of a patient, information about the patient Including at least a diameter of a trachea and a length of an intubation pathway;
   determine a recommended endotracheal tube (ETT) size including an ETT diameter and an ETT depth of insertion from the determined diameter of the trachea and the determined length of the intubation pathway; and
   display the recommended ETT size on a display device,
   wherein the electronic controller is further configured to control a computed tomography (CT) scanner to acquire the one or more images of the upper airway of the patient,
   wherein the electronic controller is configured to control the CT scanner to acquire the one or more images of the upper airway of the patient by operations including:
      controlling the CT scanner to acquire a diagnostic torso CT image at a first X-ray level;
      controlling the CT scanner to acquire an extended upper CT image extending upward from the diagnostic torso CT image at a second X-ray level that is lower than the first X-ray level; and
      combining the diagnostic torso CT image and the extended upper CT image to generate the one or more images of the upper airway of the patient.

8. An intubation assistance method comprising, using an electronic controller:
   identify, from one or more images of a patient, information about the patient including at least a diameter of a trachea and a length of an intubation pathway;
   determine a recommended endotracheal tube (ETT) size including an ETT diameter and an ETT depth of insertion from the determined diameter of the trachea and the determined length of the intubation pathway; and
   display the recommended ETT size on a display device,
   wherein determining the size of the associated ETT includes:

using an ETT model to determine a stiffness of the ETT, the identification of the length of the intubation pathway being further based on the stiffness of the ETT.

\* \* \* \* \*